(12) United States Patent
LeClair (10) Patent No.: US 7,517,430 B1
(45) Date of Patent: Apr. 14, 2009

(54) METHOD AND APPARATUS FOR THE CONTROLLED FORMATION OF CAVITATION BUBBLES

(76) Inventor: Mark L. LeClair, 25 Jesse Daniels Dr., Buxton, ME (US) 04093

( * ) Notice: Subject to any disclaimer, the term of this patent is extended or adjusted under 35 U.S.C. 154(b) by 183 days.

(21) Appl. No.: 11/175,778

(22) Filed: Jul. 5, 2005

Related U.S. Application Data

(62) Division of application No. 10/229,341, filed on Aug. 26, 2002, now Pat. No. 6,960,307.

(60) Provisional application No. 60/350,849, filed on Jan. 18, 2002.

(51) Int. Cl.
*H01B 13/00* (2006.01)
*C23C 16/00* (2006.01)

(52) U.S. Cl. ............ 156/345.3; 134/184; 134/1.3; 118/721

(58) Field of Classification Search ........... 156/345.3, 156/345.11, 345; 118/721; 134/184, 1.3
See application file for complete search history.

(56) References Cited

U.S. PATENT DOCUMENTS

| | | | |
|---|---|---|---|
| 4,231,657 A | 11/1980 | Iwamatsu | |
| 4,759,894 A | 7/1988 | McCorkle | |
| 5,057,184 A | 10/1991 | Gupta et al. | |
| 5,437,729 A | 8/1995 | Boatner et al. | |
| 5,649,556 A * | 7/1997 | Braun | 134/92 |
| 6,932,914 B2 * | 8/2005 | LeClair | 216/52 |
| 2002/0034610 A1 | 3/2002 | Perez et al. | |
| 2002/0045911 A1 | 4/2002 | Fletcher et al. | |
| 2003/0074010 A1 * | 4/2003 | Taleyarkhan | 606/128 |
| 2004/0054357 A1 | 3/2004 | O'Donnel | |
| 2005/0244301 A1 * | 11/2005 | Fletcher et al. | 422/99 |

OTHER PUBLICATIONS

Akhatov et al, Collapse and Rebound of Laser Induced Cavitation Bubble, CAV2001: Fourth International Symposium on Cavitation, California Institute of Technology, Jun. 20-23, 2001.
Ishida et al, Cavitation Bubble Behavior Near Solid Boundaries, CAV2001; Fourth International Symposium on Cavitation, California Institute of Technology, Jun. 20-23, 2001.
Blake et al, Boundary Integral Methods for Cavitation Bubbles Near Boundaries, CAV2001: Fourth International Symposium on Cavitation, California Institute of Technology, Jun. 20-23, 2001.

(Continued)

*Primary Examiner*—Sylvia R. MacArthur
(74) *Attorney, Agent, or Firm*—Lorimer Labs; D'Arcy H. Lorimer (57) ABSTRACT

The present invention discloses a method and apparatus for the directed formation of a re-entrant micro-jet formed upon the collapse of a cavitation bubble formed proximate to a work surface placed in a fluid. A mask containing an orifice, placed between the work surface and the cavitation bubble, is utilized to direct the re-entrant micro-jet to the work surface. The cavitation bubble may be formed in the desired location by focusing an energy flow proximate to the mask. The energy flow may be obtained by radiation from laser, x-ray, or electrical discharge sources.

8 Claims, 10 Drawing Sheets

OTHER PUBLICATIONS

Baghdassarain et al, Spectrum of Luminescence from Laser Induced Bubbles in Water and Cryogenic Fluids, CAV2001: Fourth International Symposium on Cavitation, California Institute of Technology, Jun. 20-23, 2001.

Tomita et al, Energy Evaluation of Schock Wave Emission and Bubble Generation by Laser Focussing in Liquid Nitrogen, CAV2001:Fourth International Symposium on Cavitation, California Institute of Technology, Jun. 20-23, 2001.

Christopher E. Brennen, Cavitation and Bubble Dynamics, Oxford U. Press, NY NY, 1995, pp. 70-76.

Christopher E. Brennen, Cavitation and Bubble Dynamics, Oxford U. Press, NY NY, 1995, pp. 70-76.

Akhatov et al, Collapse and Rebound of Laser Induced Cavitation Bubble, CAV2001; Fourth International Symposium on Caviatation, California Institute of Technology, Jun. 20-23, 2001.

Ishida et al, Cavitation Bubble Behavior Near Solid Boundaries, CAV2001: Fourth International Symposium on Cavitation, California Institute of Technology, Jun. 20-23, 2001.

Blake et al, Boundary Integral Methods for Cavitation Bubbles Near Boundaries, CAV2001: Fourth International Symposium on Cavitation, California Institute of Technology, Jun. 20-23, 2001.

Baghdassarain et al, Spectrum of Luminescence from Laser Induced Bubbles in Water and Cryogenic Fluids, CAV2001: Fourth International Symposium on Cavitation, California Institute of Technology, Jun. 20-23, 2001.

Tomita et al, Energy Evaluation of Schock Wave Emission and Bubble Generation by Laser Focussing in Liquid Nitrogen, CAV2001:Fourth International Symposium on Cavitation, California Institute of Technology, Jun. 20-23, 2001.

Presentation entitled "Cavitation and the Future of Nanotecnology", Abstract, presented at the Ninth Foresight Conference on Molecular Nanotechnology, Nov. 9-11, 2001, at the Westin Hotel, Santa Clara, CA.

Presentation entitled "Cavitation and the Future of Nanotecnology", presented at the Ninth Foresight Conference on Molecular Nanotechnology, Nov. 9-11, 2001, at the Westin Hotel, Santa Clara, CA.

* cited by examiner

| For a Pulsed Gaussian TEM00 Laser: | | | | | | | |
|---|---|---|---|---|---|---|---|
| Laser Type: | CO2 | Nd-YAG | Ruby | Dye | Dye | Excimer | X-Ray |
| Spectrum: | Far IR | Near IR | Visible (Red) | Visible (Blue) | Visible (Near UV) | Far UV | X-Ray |
| Collimated Laser Beam Radius (w1) <mm> = | 10 | 10 | 10 | 10 | 10 | 10 | 10 |
| Laser Wavelength (gamma) <um> = | 10.6 | 1.06 | 0.698 | 0.488 | 0.35 | 0.13 | 0.01 |
| Laser Focus Diameter (wo = gamma*f/(pi*w1)) <um> = | 10.8 | 1.1 | 0.71 | 0.50 | 0.36 | 0.13 | 0.01 |
| Average Cylindrical Focus Volume <cc> = | 2.8E-09 | 2.8E-12 | 7.9E-13 | 2.7E-13 | 9.9E-14 | 5.1E-15 | 2.3E-18 |
| Average Cylindrical Focus Mass <g> = | 2.8E-09 | 2.8E-12 | 7.9E-13 | 2.7E-13 | 9.9E-14 | 5.1E-15 | 2.3E-18 |
| Laser Cavitation Bubble Diameter Generated <um> = | 520 | 52 | 34 | 24 | 17 | 6.4 | 0.49 |
| Collapsed Bubble Diameter <nm> = | 5800 | 577 | 380 | 266 | 191 | 71 | 5.4 |
| Collapsed Bubble Jet Diameter <nm> = | 1200.0 | 115 | 76 | 53 | 38 | 14 | 1.1 |

*Must be greater than the wavelength of the laser

FIG. 10

| For Electric Discharge: | | | | |
|---|---|---|---|---|
| Voltage <V> | 5000 | 4000 | 3000 | 2000 |
| Capacitance <uF> = | 1 | 1 | 1 | 1 |
| Total Pulse Energy <J> = | 12.5 | 8 | 4.5 | 2 |
| Capacitor Discharge Time <usec> = | 1 | 1 | 1 | 1 |
| Cavitation Bubble Diameter Generated <mm> = | 6 | 5 | 4 | 3 |
| Collapsed Bubble Diameter <mm> = | 70 | 60 | 49 | 38 |
| Estimated Collapsed Bubble Jet Diameter <um> = | 14 | 12 | 10 | 8 |

FIG. 11

METHOD AND APPARATUS FOR THE CONTROLLED FORMATION OF CAVITATION BUBBLES

CROSS REFERENCE TO RELATED APPLICATIONS

This application is a divisional application of non-provisional application Ser. No. 10/229,341 filed Aug. 26, 2002 now U.S. Pat. No. 6,960,307 entitled METHOD AND APPARATUS FOR THE CONTROLLED FORMATION OF CAVITATION BUBBLES, which claims the benefit of provisional application No. 60/350,849 filed Jan. 18, 2002 entitled METHOD AND APPARATUS FOR THE CONTROLLED FORMATION OF CAVITATION BUBBLES, and claims benefit thereof. The aforementioned applications are herein incorporated by reference in their entirety.

BACKGROUND OF THE INVENTION

1. Field of the Invention

This invention relates generally to the formation and control of individual micron size and submicron size cavitation bubbles for use in nanofabrication operations. More particularly, embodiments of the invention teach methods and apparatus for control of a re-entrant micro-jet formed upon collapse of an individual or array of cavitation bubbles and directing the impact of the micro-jet toward a work surface with a high degree of precision.

2. Description of the Related Art

In general, the production of cavitation has been a phenomena many have tried to avoid. Cavitation in a liquid is the formation, growth, and collapse of gaseous and vapor bubbles due to the reduction of pressure below the vapor pressure of the liquid at the working temperature. Pump impellers, boat props, and similar applications experience cavitation which can produce rapid damage and erosion of surfaces. It has been well known for many years that ultrasonic cleaning devices, which function by the creation of cavitation bubbles, can produce significant surface damage to even the hardest of materials. Studies by a number of authors have revealed that one significant element in producing the damage caused by cavitation occurs when a cavitation bubble collapses in the vicinity of a surface, launching what is called a re-entrant micro-jet toward the surface. This liquid jet can produce velocities as high as 1500 m/s, and is capable of damaging the hardest materials known.

Recently, a number of applications have been developed utilizing the formation of cavitation bubbles through the use of laser light or electrical discharge. Esch et al. (U.S. Pat. No. 6,139,543) and Herbert et al. (U.S. Pat. No. 6,210,400) disclose the use of laser light introduced into a catheter device for the purpose of creating cavitation bubbles, whose expansion and collapse are utilized to pump fluids in and out of the catheter. Hammer et al. (U.S. Pat. No. 5,738,676) discloses a laser surgical probe with a special lens designed to produce the cavitation bubbles further from the end of the fiber optics, to reduce the damage formed (presumably by the re-entrant micro-jets launching into the lens on the end of the cable). Such damage was also reported by Rol et al. in "Q Switched Pulses and Optical Breakdown Generation Through Optical Fibers", *Laser and Light in Opthalmology*, Vol. 3, No. 3, 1990. Palanker (U.S. Pat. No. 6,135,998) describes a method for performing electrosurgery using sub-microsecond, high power electrical pulses are applied to an electrosurgical probe interface. The tool described by Palanker provides a cutting force by both the plasma generated by the electrical arc and shock waves produced by collapsing cavitation bubbles.

In each of the prior art references cited above, there has been no attempt to control the direction and impact of the powerful micro-jets formed upon the collapse of the cavitation bubbles created when highly focused energy is introduced into a liquid. Without such control, concern of collateral damage cannot be avoided, especially when such tools are used in the human body in a medical application.

Recently as well, there has been a significant interest generated in the field of nanotechnology, for methods needed to fabricate micron and submicron devices and nanomachines. There are very few fabrication tools available that can cut, drill, peen, deform, or otherwise modify features of a surface on a submicron to nanometer scale. Much of the technology developed by the semiconductor industry requires the fabrication of structures utilizing photolithographic processing. This technology is not as flexible as may be required, and will have certain difficulties when applied to biological nanotechnology systems. Advancing the state of the art required by nanotechnology applications will require fabrication technologies operating at least 1 to 2 orders of magnitude below that capable in the semiconductor process arena.

The prior state of the art therefore has yet to provide a fabrication technology capable of operating in the nanometer region by harnessing the powerful phenomena of the re-entrant micro-jet formed during the collapse of a precisely located cavitation bubble.

SUMMARY OF THE INVENTION

An apparatus for the controlled formation of cavitation bubbles in accordance with the present invention includes a mask immersed in a liquid proximate to a work surface, wherein the mask has a first surface opposing and separate from the work surface, a second surface opposing the first surface, and at least one aperture extending from the first surface to the second surface. The apparatus further includes an energy source capable of generating an energy flow in the liquid sufficient to create at least one cavitation bubble, the cavitation bubble being located opposite the second surface proximate to the aperture, wherein a collapse of the cavitation bubble creates a re-entrant micro-jet directed through the aperture at the work surface.

DETAILED DESCRIPTION OF THE PREFERRED EMBODIMENT(S)

The sequence illustrated in FIGS. 1A-E illustrate the formation of a re-entrant micro-jet from the formation and collapse of a cavitation bubble in accordance with the present invention.

Figure 1A:
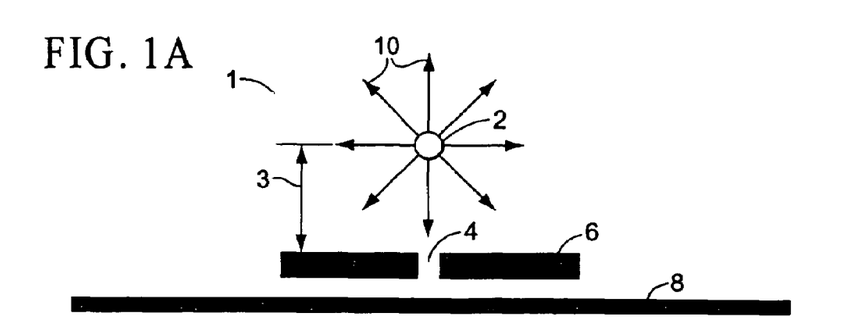
FIG. 1A is a schematic view of a cavitation initiation volume in accordance with one embodiment of the present invention.

FIG. 1A is a schematic view of a cavitation initiation volume in accordance with one embodiment of the present invention. The energy from a cavitation initiation device (not shown) is focused into a volume 2 aligned over aperture 4, at a nominal distance 3 from aperture mask 6 placed in proximity to a work piece surface 8. The intense energy focused into the small focus volume 2 is absorbed by the fluid 1, causing rapid boiling and expansion of vaporized gasses. Arrows 10 represent the rapid movement of the gas liquid boundary of the cavitation bubble formed in volume 2. Energy sources may include, but are not limited to: lasers, x-ray sources, ultrasound, electrical discharge, and positrons.

Figure 1B:
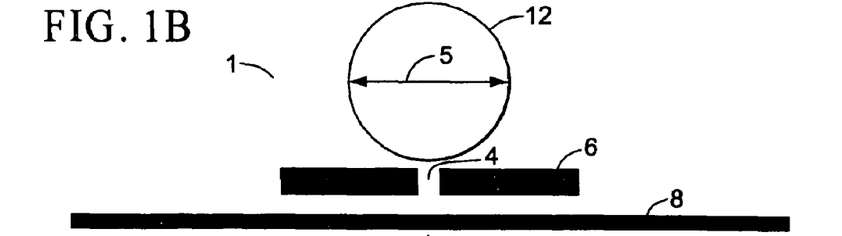
FIG. 1B is a schematic view of a fully expanded cavitation bubble in accordance with one embodiment of the present invention.

FIG. 1B is a schematic view of a fully expanded cavitation bubble in accordance with one embodiment of the present invention. Cavitation bubble 12, formed from the rapid expansion of vaporized fluid in volume 2 and the momentum of liquid moving away from the center of the focus volume 2, has reached its maximum diameter 5. Typically, the maximum diameter 5 of the fully expanded cavitation bubble 12 is approximately 10 to 50 times the diameter of the focus volume 2 shown in the previous FIG. 1A. Gas pressure inside fully expanded cavitation bubble 12 may be as low as the vapor pressure of fluid 1 at it's bulk temperature. The pressure of the surrounding fluid 1, typically at 1 atmosphere absolute or higher, creates a pressure differential on the outer surface of the bubble 12, driving its subsequent collapse. For fluids 1 such as water at 1 atmosphere and 25° C., the pressure differential can exceed 700 torr.

Figure 1C:
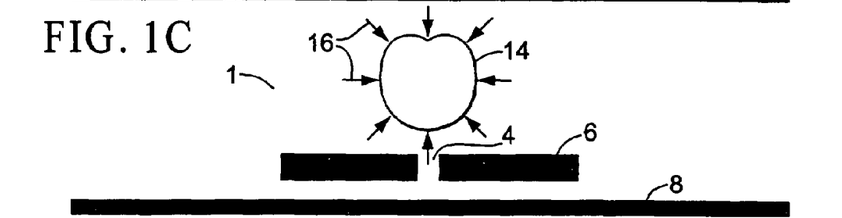
FIG. 1C is a schematic view of a collapsing cavitation bubble in accordance with one embodiment of the present invention.

FIG. 1C is a schematic view of a collapsing cavitation bubble in accordance with one embodiment of the present invention. Cavitation bubble 14 has begun a rapid collapse illustrated by rapid inner movement of its outer surface and arrows 16.

Figure 1D:
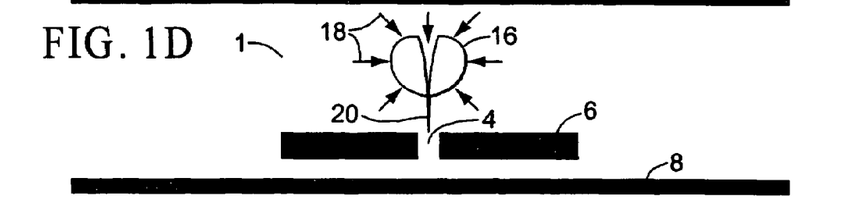
FIG. 1D is a schematic view of the initial formation of a re-entrant micro-jet induced by the collapsing cavitation bubble in accordance with one embodiment of the present invention.

FIG. 1D is a schematic view of the initial formation of a re-entrant micro-jet 20 induced by the collapsing cavitation bubble 16 in accordance with one embodiment of the present invention. Re-entrant micro-jet 20 is launched through aperture 4 toward work surface 8. Aperture mask 6 serves to block subsequent shock waves produced by collapsing cavitation bubble 16 from work surface 8, allowing only the high velocity, focused re-entrant micro-jet to impact the surface.

Figure 1E:
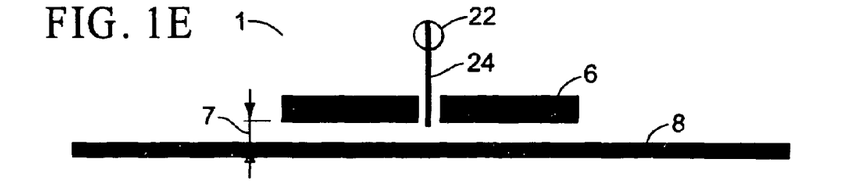
FIG. 1E is a schematic view of a re-entrant micro-jet directed through an aperture to a work surface in accordance with one embodiment of the present invention.

FIG. 1E is a schematic view of a re-entrant micro-jet directed through an aperture to a work surface in accordance with one embodiment of the present invention. The fully formed re-entrant micro-jet 24 impacts the work surface 8 through aperture 4. The re-entrant micro-jet 24 may impact the work surface with velocities as high as 1500 meters/second, and is capable of removing material from the hardest surfaces known, such as diamond. These jets may be used to cut, machine, drill through, erode or deform features on the work surface 8. The diameter of the jets are determined by the size of the cavitation bubble 12 formed, which in turn is determined by the dimensions of the focus volume 2 and the level of energy introduced into said focus volume. As will be illustrated in subsequent figures, the re-entrant micro-jet 24 diameters may vary from about 1 micron to about 1 nanometer for focused laser and x-ray energy sources. Electric discharge sources may produce re-entrant micro-jet diameters on the order of 10 to 15 microns. The velocity of the re-entrant micro-jet through the aperture is primarily determined by the distance 3 of the focus volume 2 to the aperture mask 6, and can vary from ½ the expanded bubble diameter 5 to about 6 times the expanded bubble diameter 5, with the optimum distance being approximately 3 expanded bubble diameters 5. The impact force of the re-entrant micro-jet 24 on work surface 8 may be adjusted by altering the distance 7 between the aperture mask 6 and the work surface 8. At a given jet velocity (or fixed distance between the focus volume 2 and aperture mask 6), the impact force will vary inversely with the distance 7, in a range from approximately zero to 6 expanded bubble diameters 12, but preferably in a range from zero to 4 bubble diameters 12. The diameter of the aperture 4 can be in a range from about 1% to 30% of the expanded bubble diameter. The re-entrant micro-jet diameter is on the order of about 0.2% of the expanded bubble diameter 12.

The aperture mask 6 and aperture 4 play an essential role in directing and controlling the action of the re-entrant micro-jet 24. Without the aperture mask, the collapse of the cavitation bubble (12, 14, 16) would still launch a re-entrant micro-jet toward the surface 8, but the location of impact and the force imparted would be unpredictable, especially on a nanometer scale. In addition, the aperture mask tends to keep shock waves created in the expansion and contraction stages from damaging the surface 8. Accurate placement of the aperture and the focus volume allow nanometer scale precision cutting, punching, peening, drilling, or deforming operations on sub-micron scale features of the work surface. Many prior art applications are capable of accurate placement of the initial focus volume, but do little or nothing to control the shock waves and re-entrant micro-jet formed upon collapse of the cavitation bubble.

Figure 2:
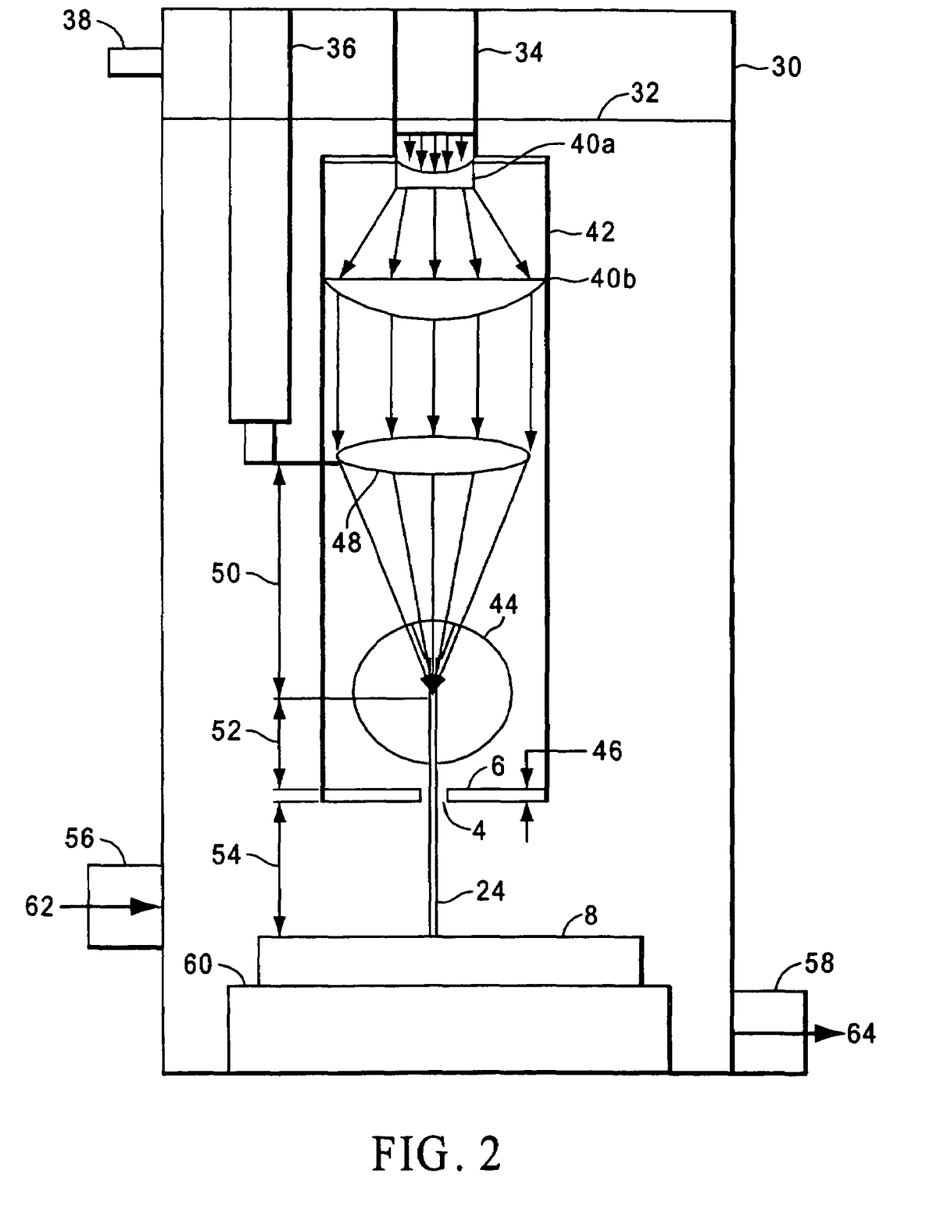
FIG. 2 is a schematic view of a lens focused laser apparatus for producing cavitation induced re-entrant micro-jets in accordance with another embodiment of the present invention.

FIG. 2 is a schematic view of a lens focused laser apparatus for producing cavitation induced re-entrant micro-jets in accordance with another embodiment of the present invention. Sealed tank 30 contains liquid filled to a level 32. Various liquids can be used, but high purity water (>100 k ohms resistivity) is preferred. The beam from laser 34 is directed to lenses 40a and 40b to collimate the beam, which is then focused by lens 48 at a focal distance 50. Beam focus positioner 36 determines the location of the focus volume 2 relative to the aperture mask 6, at a distance 52. Work surface 8 is moved by precision XYZ stage 60, to adjust the distance from aperture mask 6 to the work surface, as well as locate the specific area on the work surface to be impacted by the jet 24. Recall from previous FIGS. 1A-E, that the position of the focus volume determines the location of the subsequent cavitation bubble 44 and re-entrant micro-jet 24. Fluid inlet 56 and outlet 58 are utilized to provide a constant flushing of the fluid in the tank 30, in part to remove any debris produced by the machining occurring on the work surface 8. This debris may negatively impact the absorption of subsequent laser light pulses in the focus volume, as well as potentially contaminate the surface with entrained particle matter introduced into the re-entrant micro-jet. For similar reasons, it may be desirable (although not essential) to filter the incoming fluid stream 62 to remove any particulate contamination. Tank 30 is equipped with a pressure transducer 38 to monitor and control the back pressure. For a sealed tank as shown, this may be done simply by raising the inlet pressure of incoming fluid stream 62 with respect to the outlet pressure of outlet stream 64, by choking the outlet flow until the tank ambient pressure is as desired, the re-equilibrating the flows once again.

Figure 3:
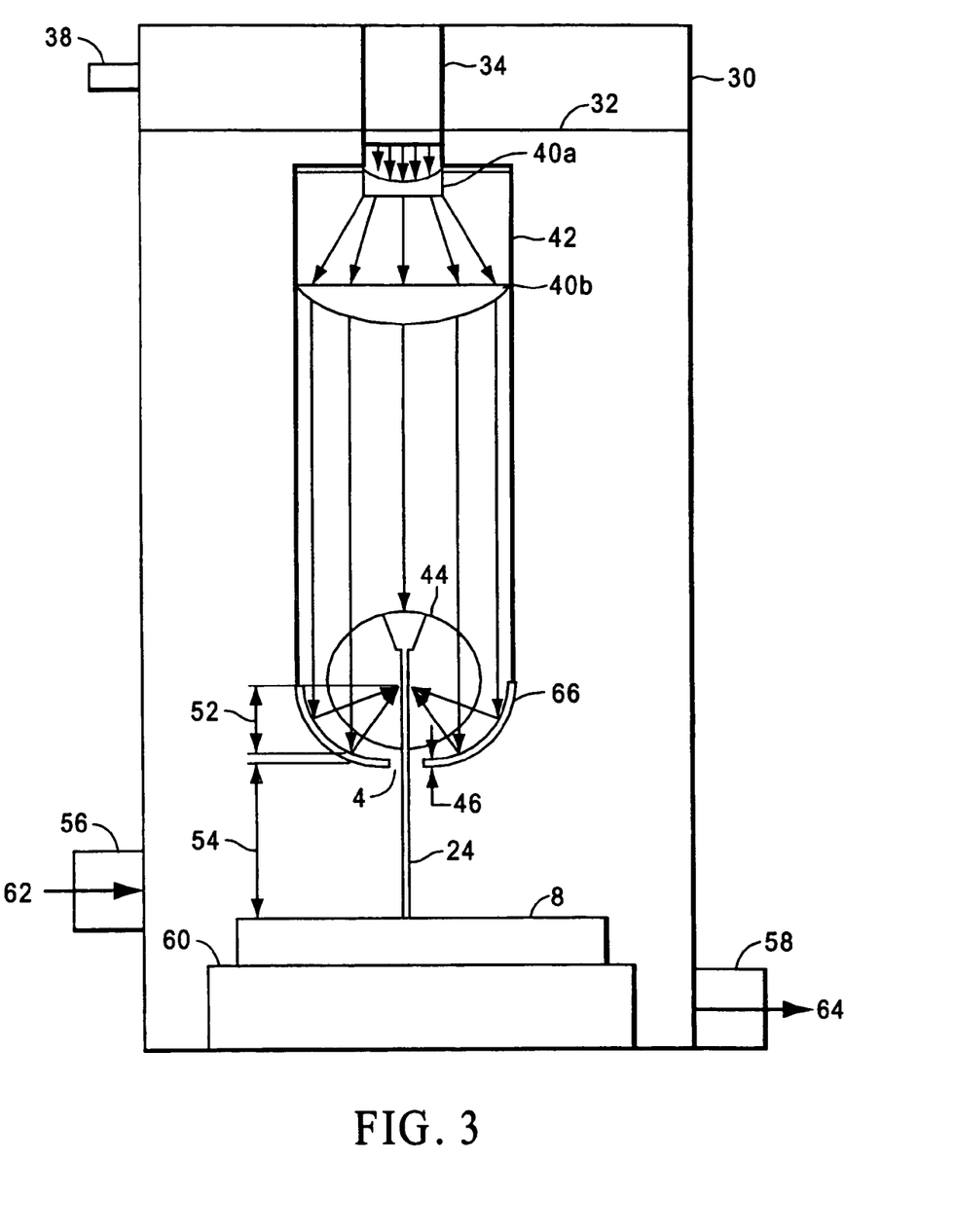
FIG. 3 is a schematic view of a parabolic mirror focused laser apparatus for producing cavitation induced re-entrant micro-jets in accordance with another embodiment of the present invention.

FIG. 3 is a schematic view of a parabolic mirror focused laser apparatus for producing cavitation induced re-entrant micro-jets in accordance with another embodiment of the present invention. As was shown in FIG. 2, laser 34 directs a beam into collimator lenses 40a and 40b. The collimated beam is directed onto a parabolic mirror 66, which also contains the aperture 4. Parabolic mirror 66 focuses the collimated laser beam to a focus volume at a distance 52 from the aperture. In this embodiment, distance 52 is fixed by the curvature parameters of the parabolic mirror 66, and therefore the velocity of the re-entrant micro-jet 24 is also fixed. An XYZ stage 60 determines the distance 54 from the aperture to the work surface, as well as the XY coordinates of the area to be worked on. All other features are as described in FIG. 2.

Figure 4:
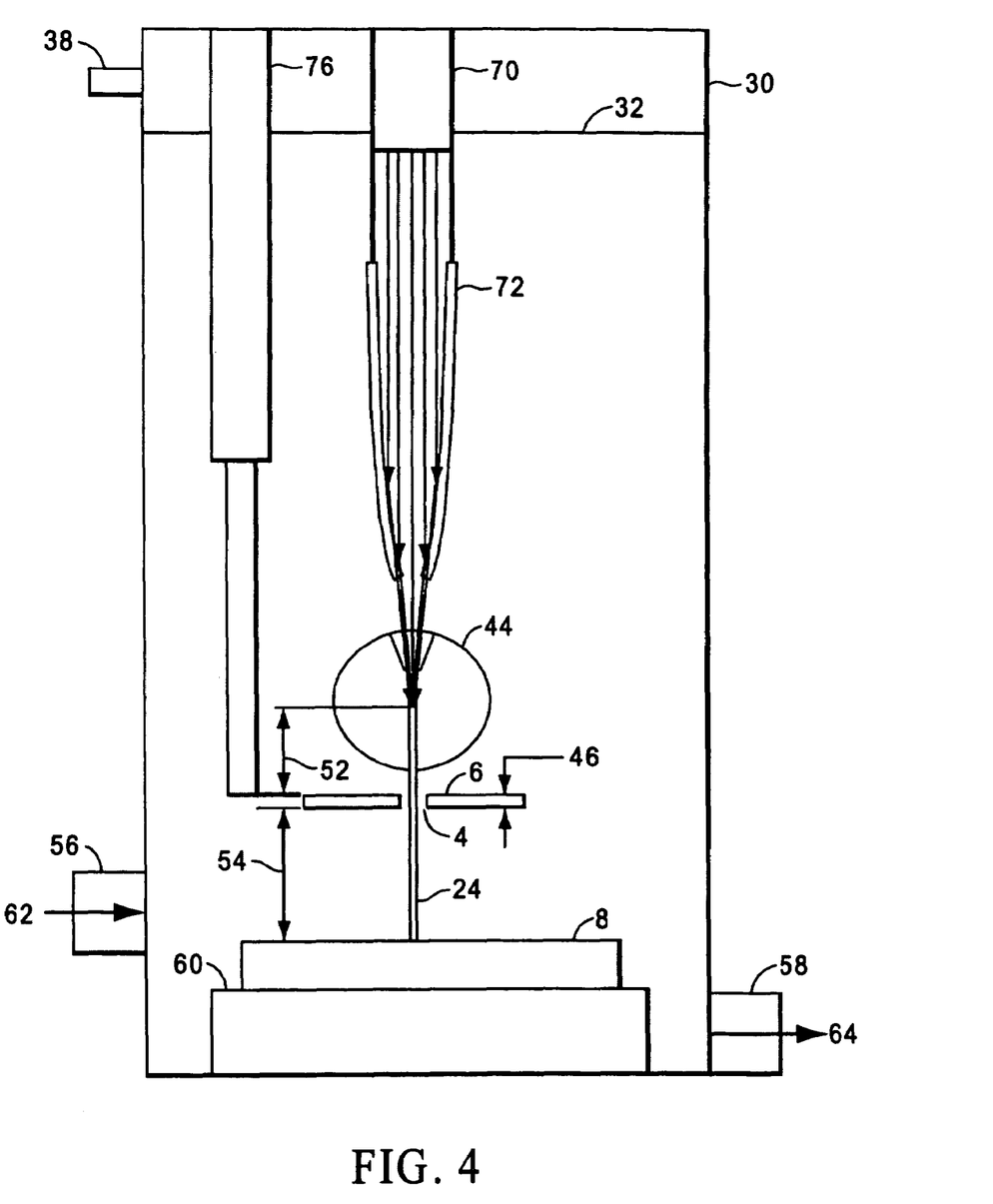
FIG. 4 is a schematic view of a lens focused x-ray source apparatus for producing cavitation induced re-entrant micro-jets in accordance with another embodiment of the present invention.

FIG. 4 is a schematic view of a lens focused x-ray source apparatus for producing cavitation induced re-entrant micro-jets in accordance with another embodiment of the present invention. X-ray source 70 directs a beam into x-ray lens 72, which focuses and concentrates the x-ray beam into a focus volume at a distance 52 from an aperture mask 6. Aperture positioner 76 adjusts distance 52 to alter re-entrant micro-jet velocity through the aperture 4. Dimension 54, or the distance of the aperture mask to the work surface 8 is adjusted by XYZ stage as has been previously described. All other features are as described in FIG. 2.

Figure 5:
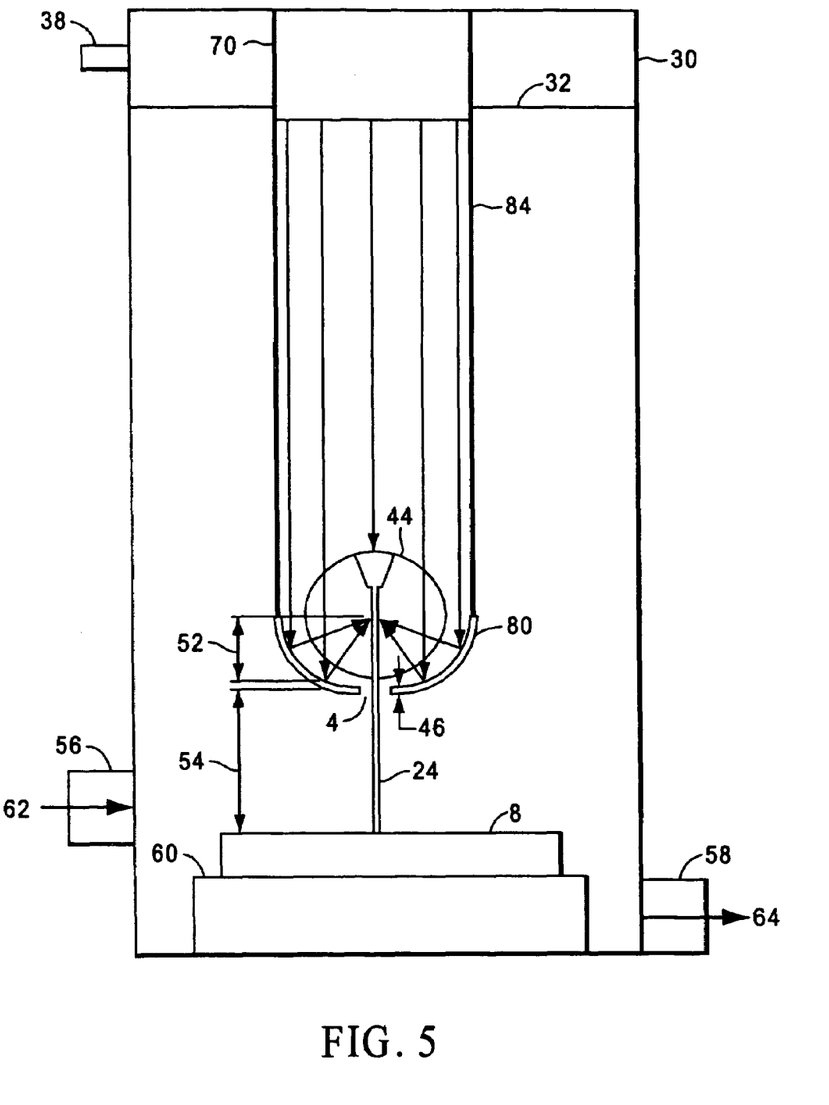
FIG. 5 is a schematic view of a parabolic mirror focused x-ray source apparatus for producing cavitation induced re-entrant micro-jets in accordance with another embodiment of the present invention.

FIG. 5 is a schematic view of a parabolic mirror focused x-ray source apparatus for producing cavitation induced re-entrant micro-jets in accordance with another embodiment of the present invention. X-ray source 70 directs a beam onto parabolic x-ray mirror 80 containing an aperture 4. The x-ray beam is focused into a focus volume at a distance 52 from the aperture 4. The dimension 54 between the aperture mask 6 and work surface 8 is adjusted by the XYZ stage 60. In this embodiment, distance 52 is fixed by the curvature parameters of the parabolic mirror 80, and therefore the velocity of the re-entrant micro-jet 24 is also fixed.

Figure 6:
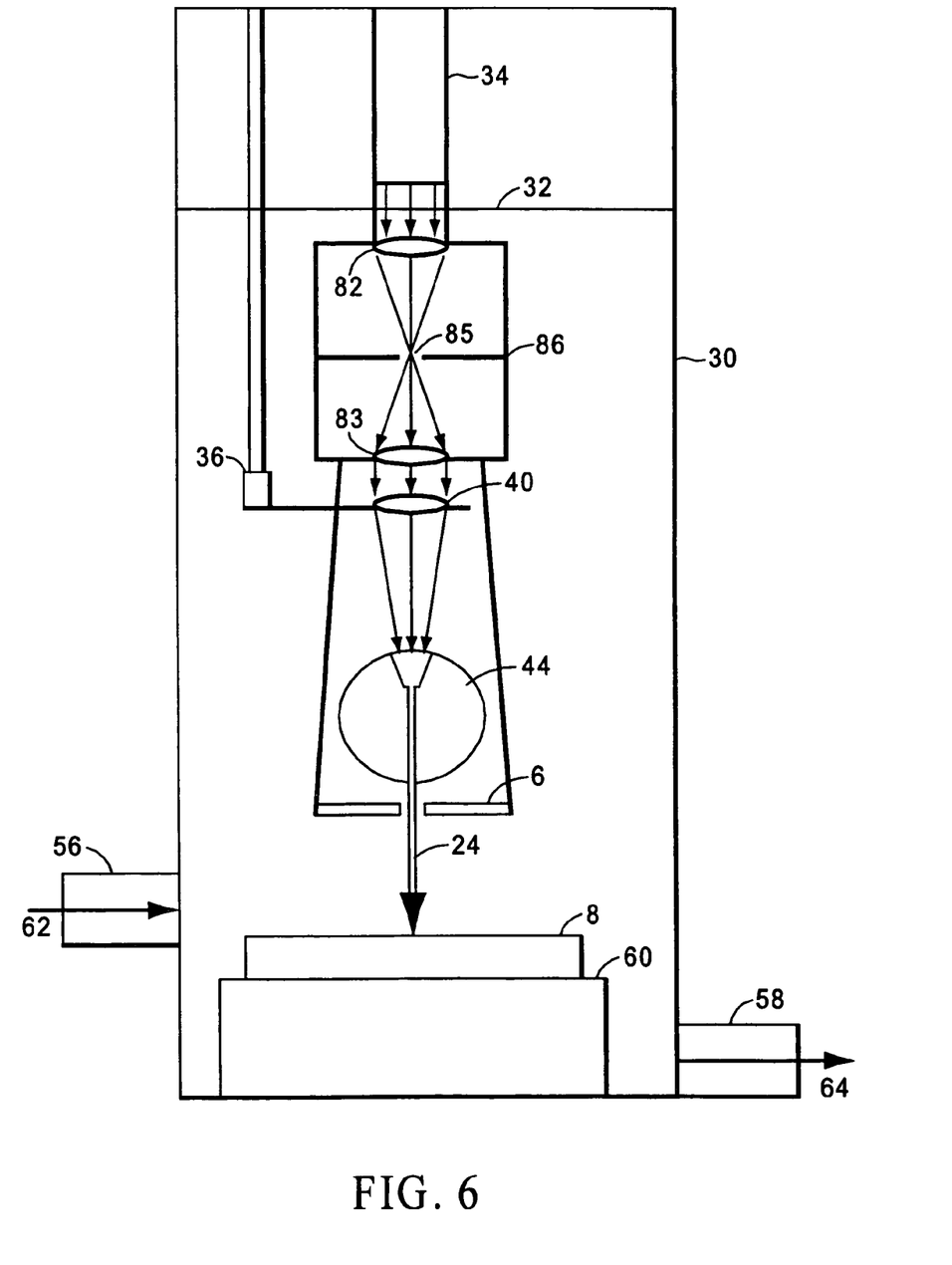
FIG. 6 is a schematic view of spatial filter added to a lens focused laser apparatus for producing cavitation induced re-entrant micro-jets in accordance with another embodiment of the present invention.

FIG. 6 is a schematic view of spatial filter added to a lens focused laser apparatus for producing cavitation induced re-entrant micro-jets in accordance with another embodiment of the present invention. Spatial filter 86 can be optionally added to the previously described embodiments to further clean up the laser beam or x-ray beam to allow smaller focus volumes. The spatial filter 86 comprises a entrance lens 82, a pinhole 85, and an exit lens 83. Exit lens 83 and lens 40 makes up part of the collimator lens pair as shown in previous figures.

Figure 7:
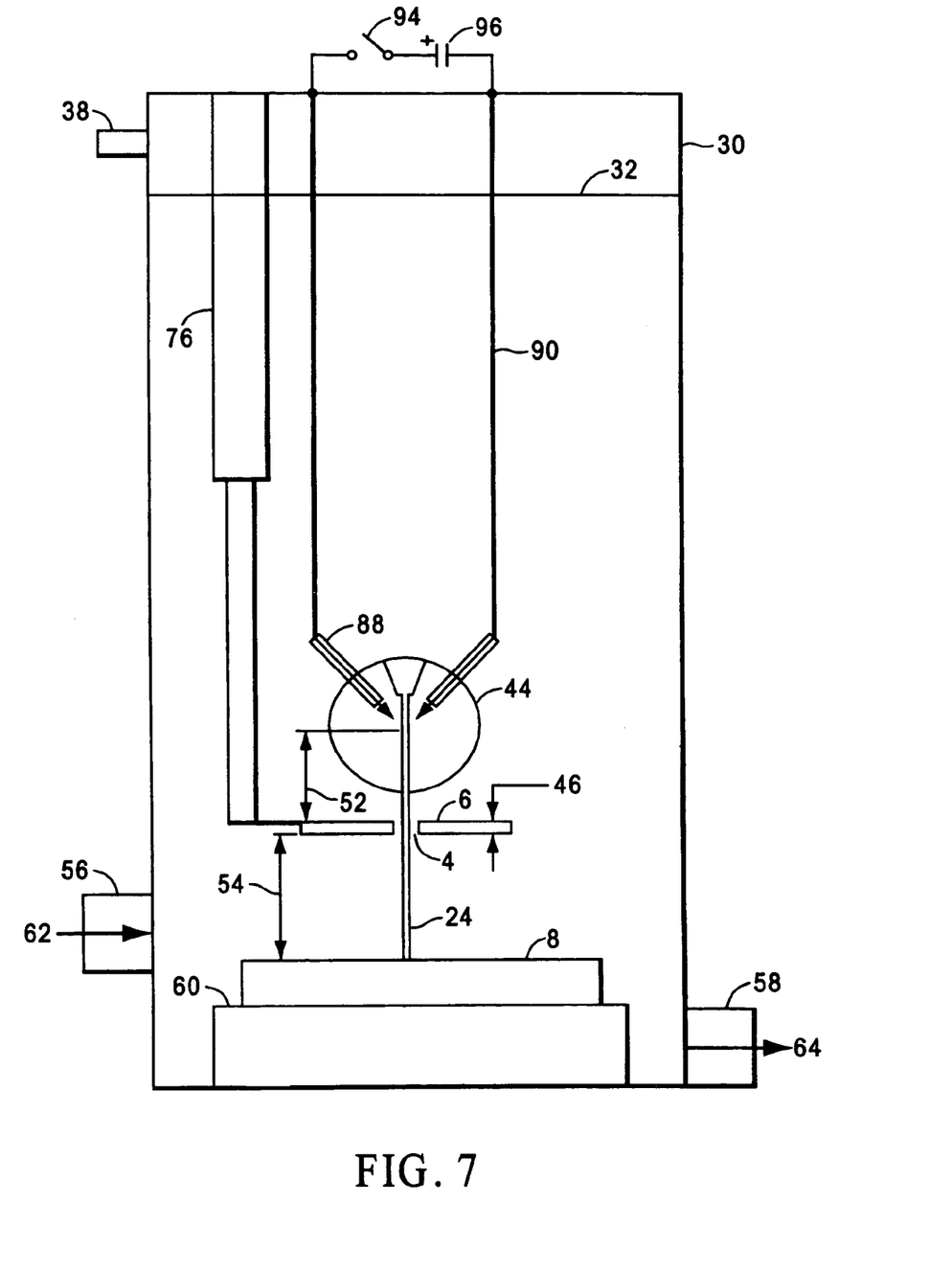
FIG. 7 is a schematic view of an electric discharge apparatus for producing cavitation induced re-entrant micro-jets in accordance with another embodiment of the present invention.

FIG. 7 is a schematic view of an electric discharge apparatus for producing cavitation induced re-entrant micro-jets in accordance with another embodiment of the present invention. A positive electrode 88 and negative electrode 90 are immersed in fluid 32 and positioned to generate an arc at a position a distance 52 above aperture mask 6. Actuator 76 adjusts dimension 52 to position the focus volume a known distance from the aperture mask 6. The arc is created by rapid discharge of capacitor 96 through switch 94. Full circuit details are not shown in FIG. 7, but are well known to those skilled in the art. Capacitor 96 is a low inductance, high voltage device as is used in pulse lasers and flash tubes. The rapid discharge and subsequent transient arc create a cavitation bubble 44 as illustrated in FIGS. 1A-E.

Figure 8:
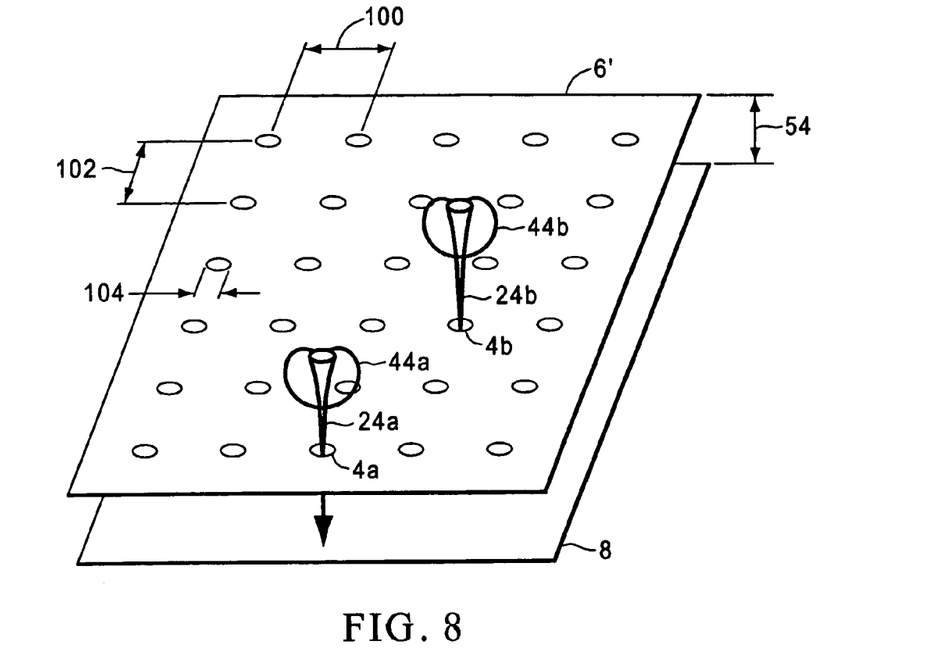
FIG. 8 is an apparatus for the production of an array of cavitation induced re-entrant micro-jets in accordance with another embodiment of the present invention.

FIG. 8 is an apparatus for the production of an array of cavitation induced re-entrant micro-jets in accordance with another embodiment of the present invention. Work surface 8 is placed parallel to an aperture mask 6' containing a plurality of apertures. Cavitation bubbles 44a, 44b (only two are shown for clarity) are formed directly over each aperture in the array by any number of techniques, as previously discussed, such that the re-entrant micro-jets 24a, 24b formed following the collapse of the cavitation bubbles are directed through the apertures 4a, 4b normal to the surface 6' and impact work surface 8. The cavitation bubbles may be formed simultaneously or sequentially, or in some other pattern (such as every other aperture, every two apertures, etc.). If the cavitation bubbles 44 are formed over each aperture simultaneously, then the aperture spacing dimensions 100 and 102 must be determined such that they are at least 6 expanded bubble diameters 12 long. These dimensions may be shortened, for example, to 3 expanded bubble diameters 12 if the cavitation bubbles are formed over every other aperture, as long as there remains at least 6 fully expanded bubble diameters between any two cavitation bubbles in the array being formed simultaneously. For cavitation bubble spacing closer than the 6 expanded bubble diameters, there is some probability (increasing with decreasing bubble spacing) that the re-entrant micro-jets produced on collapse of the adjacent cavitation bubbles will be directed toward each other, as opposed to being directed through the apertures. This is undesirable. Alternatively, aperture mask 6' may be moved relative to work surface 8 to place the impact location of the various re-entrant micro-jets in any desired location on the work surface.

The array of cavitation bubbles may be produced by a number of techniques in accordance with the present invention. For example, an array of lasers as illustrated in FIGS. 2, 3, and 6 may be employed. Or a single laser having a fiber optic array employing multiple collimators located over each aperture 4a, 4b may also be used. Additionally, a single laser and collimator may be scanned over the aperture array such that each "firing" of the pulse laser produces a focus volume of light energy over the appropriate aperture position. The same process may also be utilized with the x-ray source. Additionally, the aperture location may be moved by XYZ stage 60 while holding the aperture mask 6' fixed over the work surface 8, utilizing a single laser or x-ray source. For the case of the electrical discharge, a multiple electrode array may be used, or the array may be positioned under a single electrode pair via the XYZ stage. An array of cavitation bubbles may also be produced by ultrasound techniques. It is well known to those skilled in the art, that many ultrasound transducers produce a three dimensional array of cavitation bubbles in a tank of fluid corresponding to a standing wave pattern of sound waves in the fluid. By creating and positioning such a standing wave pattern over the aperture mask 6', cavitation bubbles formed due to the ultrasound will collapse, directing the previously described re-entrant micro-jets through the apertures to the work surface. Not every cavitation bubble produced in the standing wave field need be located over an aperture. Those that are not will simply launch their respective jets against the mask 6'. It is important that no cavitation bubbles are formed between the mask 6' and the work surface 8. These bubble may damage the surface since the impact of their jets would uncontrolled and potentially misdirected. The properties of the ultrasound generated cavitation bubbles should conform to previously determined requirements as discussed in FIG. 1E.

Figure 9:
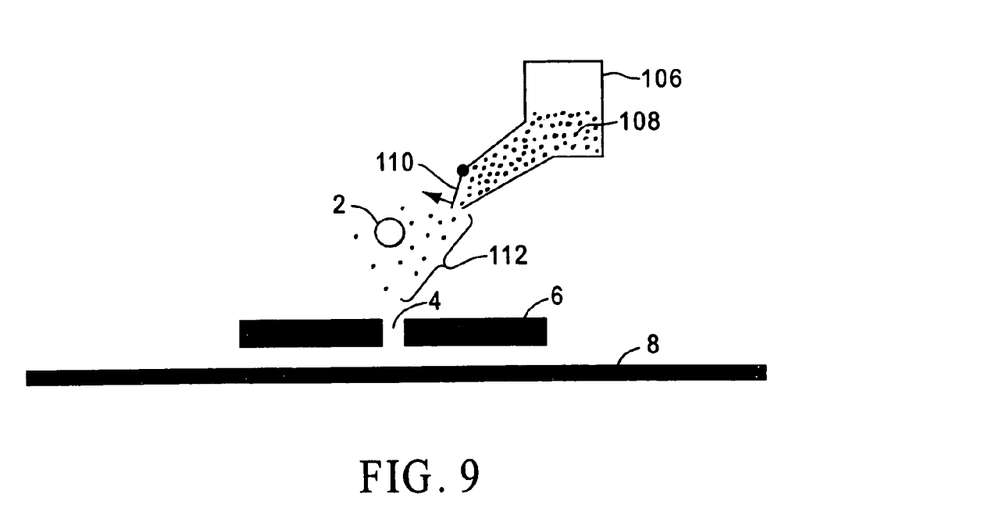
FIG. 9 is a schematic view of an apparatus for the welding of small particles in a cavitation induced re-entrant micro-jet in accordance with another embodiment of the present invention.

FIG. 9 is a schematic view of an apparatus for the welding of small particles in a cavitation induced re-entrant micro-jet in accordance with another embodiment of the present invention. Introduction of particulate matter 112 into the re-entrant micro-jet may result in the welding of the particles to each other and/or to the work surface 8. Small particles 108 stored in a container 106 are released into solution via valve 110 in the vicinity of the focus volume 2, where a cavitation bubble will be nucleated, as previously described. Particles 108 may be stored in a dry form, but preferably are mixed and suspended in a compatible fluid. Once in solution, these particles 112 will accumulate at the gas liquid interface of the cavitation bubble, and may be entrained into the re-entrant micro-jet as the cavitation bubble collapses. The very high impact forces of the micro-jet hitting the work surface causes the welding of these particles to each other and the work surface 8. This process may be used to build microstructures of various types of materials on the work surface. One application of importance would include the construction of photo resist masks for micro and nano circuit fabrication. Since photo lithography is not required for this process, the lower limits imposed by that process can be easily exceeded. The fabrication of submicron and nano scale particles is well known to those skilled in the art, as is the technology for suspending such particles in a fluid. By translating work surface 8 under aperture 4 while sequentially forming a series of cavitation bubbles 2, many types of submicron layer structures can be built. The materials making up these structures can also vary considerably, and may include polymers, metals, and inorganic ceramic materials. Some of these materials may have superior etch, resist properties that conventional organic films used today do not posses. Additionally, cavitation welded films may not need curing and baking as is required for conventional polymer photo resists.

Figure 10:
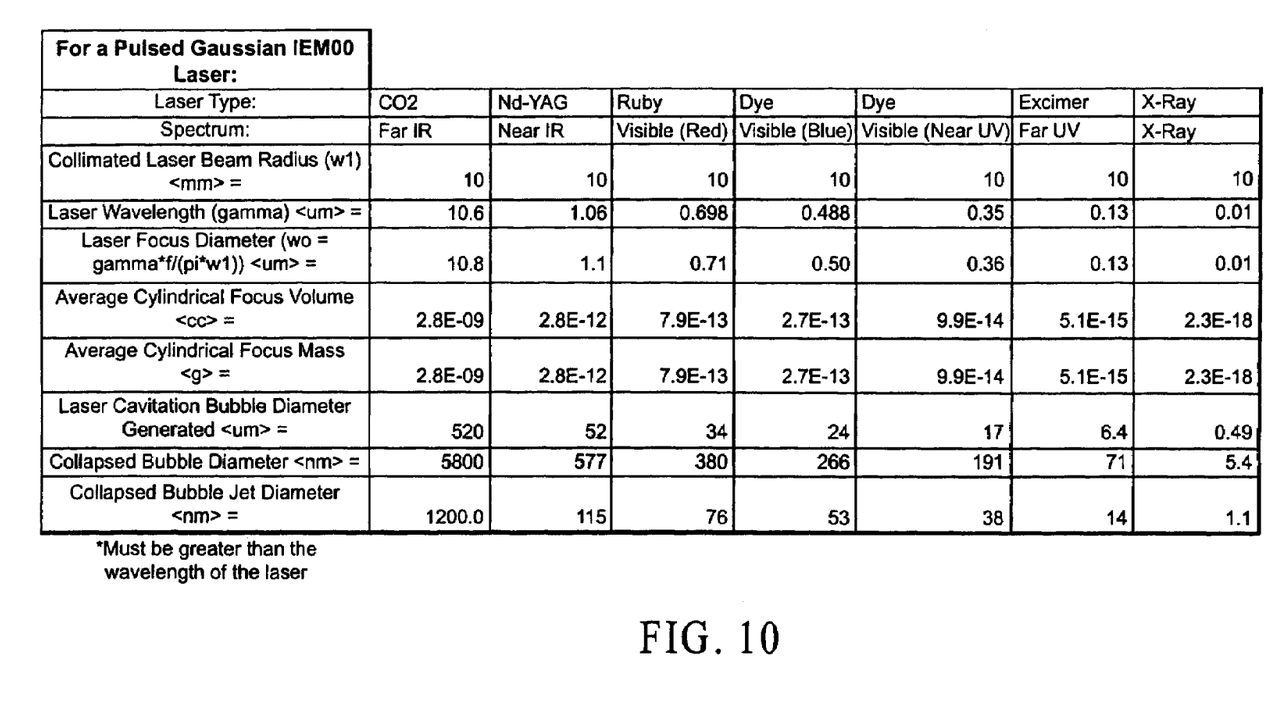
FIG. 10 is a table of parameters for the application of various pulsed Gaussian TEMOO lasers for a number of embodiments in accordance with the present invention.

FIG. 10 is a table of parameters for the application of various pulsed Gaussian TEM00 lasers for a number of embodiments in accordance with the present invention. In this table, the relationships between various laser parameters (such as laser type, spectrum of the emitted radiation and wavelength, collimated beam radius, focus diameter, and cylindrical focus volume) and the resulting cavitation bubble parameters (such as the cavitation bubble diameter and the re-entrant microjet diameter) are shown. All parameters are normalized to a collimated laser beam diameter of 10 mm. This dimension was chosen for convenience, and does not imply that collimated laser beams of larger or smaller dimensions are not applicable. In one example, a $CO_2$ laser beam of 10 mm producing an infra-red wavelength of 10.6 microns is focused to a 10.8 micron diameter in the fluid. This focused beam results in a control volume $2.8 \times 10^{-9}$ cm$^3$, generating a cavitation bubble 520 microns in size at maximum diameter. After collapse, this cavitation bubble produces a re-entrant micro-jet of 1200 nanometers in diameter. In a second example, an excimer laser beam of 10 mm producing an ultra-violet wavelength of 0.13 microns is focused to a 0.13 micron diameter in the fluid. This focused beam results in a control volume $5.1 \times 10^{-15}$ cm$^3$, generating a cavitation bubble 6.4 microns in size at maximum diameter. After collapse, this cavitation bubble produces a re-entrant micro-jet of 14 nanometers in diameter. In yet a third example, an x-ray beam of 10 mm producing an x-ray wavelength of 0.01 microns is focused to a 0.01 micron diameter in the fluid. This focused beam results in a control volume $2.3 \times 10^{-18}$ cm$^3$, generating a cavitation bubble 0.49 microns in size at maximum diameter. After collapse, this cavitation bubble produces a re-entrant micro-jet of 1.1 nanometer in diameter. As can been seen from the aforementioned examples, re-entrant micro-jets ranging over 3 orders of magnitude in diameter can be produced by changing the type of laser energy used to create the cavitation bubble, and can produce the smallest jets on the order of 1 nanometer in diameter.

Figure 11:
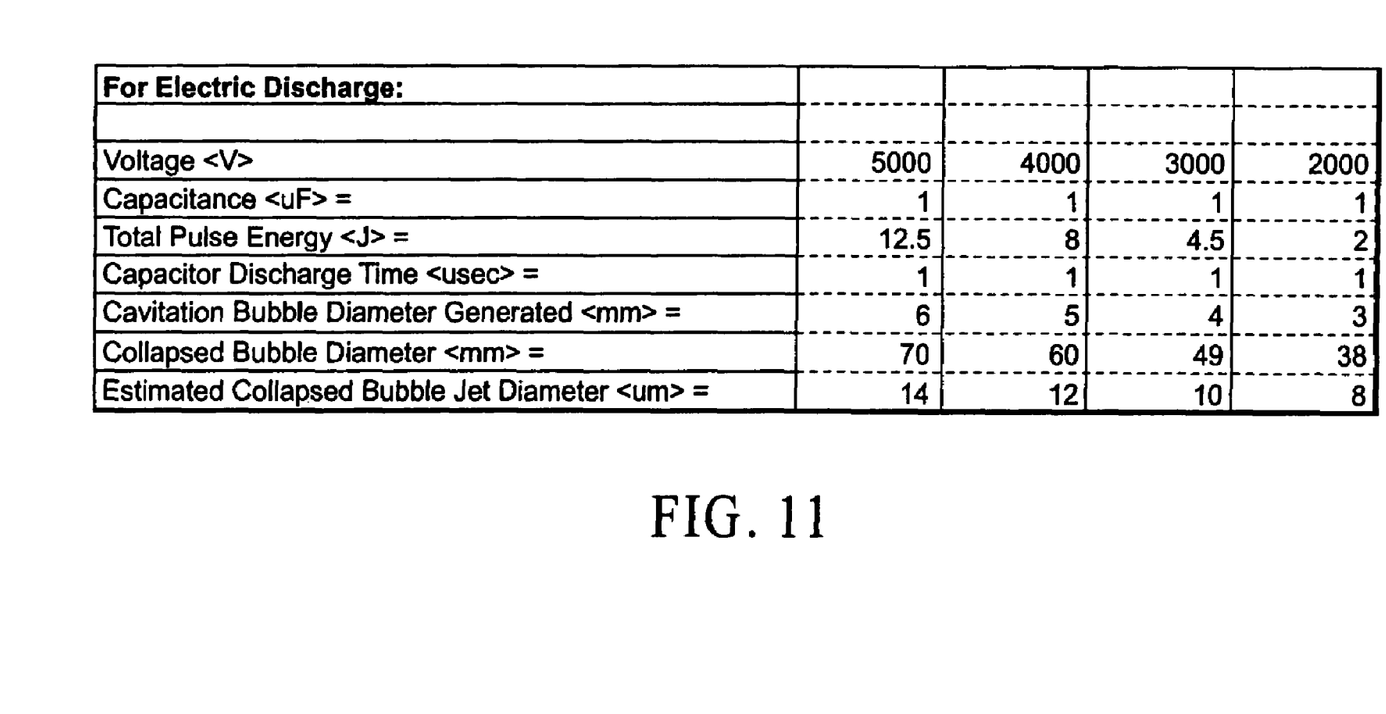
FIG. 11 is a table of parameters for the application of an electric discharge for one embodiment in accordance with the present invention.

FIG. 11 is a table of parameters for the application of an electric discharge for one embodiment in accordance with the present invention. For convenience, the data presented is based on the discharge of a 1 micro Farad capacitor. Capacitor values greater or smaller than this value are also equally applicable. In one example, the 1 micro Farad capacitor is charged to 5000 volts and discharged into the fluid generating a cavitation bubble 6 mm in diameter, creating a re-entrant micro-jet of approximately 14 microns in diameter. In a second example, the 1 micro Farad capacitor is charged to 2000 volts and discharged into the fluid generating a cavitation bubble 3 mm in diameter, creating a re-entrant micro-jet of approximately 8 microns in diameter.

The invention claimed is:

1. An apparatus for the controlled formation of cavitation bubbles comprising:
   a mask immersed in a liquid, proximate to a work surface, wherein said mask has
      a first surface opposing said work surface and separate from said work surface,
      a second surface opposing said first surface, and
      at least one aperture extending from said first surface to said second surface; and,
   an energy source capable of generating an energy flow in said liquid sufficient to create at least one cavitation bubble, said at least one cavitation bubble being located opposite said second surface proximate to said at least one aperture, wherein a collapse of said at least one cavitation bubble creates a re-entrant micro-jet directed through said at least one aperture at said work surface.

2. The apparatus for the controlled formation of cavitation bubbles as recited in claim 1 wherein said energy source is a laser.

3. The apparatus for the controlled formation of cavitation bubbles as recited in claim 2 wherein said energy flow is obtained by focusing radiation from said laser by lenses.

4. The apparatus for the controlled formation of cavitation bubbles as recited in claim 2 wherein
    said second surface is a curved reflector facing said laser; and
    said energy flow is obtained by focusing radiation from said laser by said curved reflector to a focal point proximate to said at least one aperture.

5. The apparatus for the controlled formation of cavitation bubbles as recited in claim 2 wherein said laser is chosen from among a group consisting of: a $CO_2$ laser, a Nd-YAG laser, a dye laser, a ruby laser, and an excimer laser.

6. The apparatus for the controlled formation of cavitation bubbles as recited in claim 1 wherein said energy source is an x-ray source.

7. The apparatus for the controlled formation of cavitation bubbles as recited in claim 6 wherein said energy flow is obtained by focusing radiation from said x-ray source by x-ray lenses.

8. The apparatus for the controlled formation of cavitation bubbles as recited in claim 6 wherein
    said second surface is a curved reflector facing said x-ray source; and
    said energy flow is obtained by focusing radiation from said x-ray source by said curved reflector to a focal point proximate to said at least one aperture.

* * * * *